United States Patent [19]
Hofmockel et al.

[11] 4,057,733
[45] Nov. 8, 1977

[54] DENTAL X-RAY DIAGNOSTIC INSTALLATION

[75] Inventors: Dieter Hofmockel, Erlangen; Ulrich Grassmé, Nurnberg; Johannes Seissl, Erlangen-Buckenhof; Ernst Otto Fleer, Bensheim-Auerbach, all of Germany

[73] Assignee: Siemens Aktiengesellschaft, Berlin & Munich, Germany

[21] Appl. No.: 657,296

[22] Filed: Feb. 11, 1976

[30] Foreign Application Priority Data

Feb. 17, 1975  Germany .............................. 2506630

[51] Int. Cl.² ............................................... G03B 41/16
[52] U.S. Cl. .................................... 250/491; 250/490; 250/521; 250/523
[58] Field of Search ............... 250/490, 491, 521, 522, 250/523, 479, 439 P, 369

[56] References Cited

U.S. PATENT DOCUMENTS

| 2,946,892 | 7/1960 | Bas Taymaz | 250/439 P |
| 2,976,417 | 3/1961 | Freeman | 250/439 P |
| 3,622,785 | 11/1971 | Irwin | 250/416 TV |
| 3,752,990 | 8/1973 | Fischer | 250/491 |

Primary Examiner—Craig E. Church
Attorney, Agent, or Firm—Hill, Gross, Simpson, Van Santen, Steadman, Chiara & Simpson

[57] ABSTRACT

A dental X-ray diagnostic installation in which an X-ray tube has an X-ray image intensifier associated therewith, and that means are provided which permit an alignment of its inlet screen with the focus of the X-ray tube. The X-ray image intensifier, during the carrying out of radioscopies, receives the X-radiation emanating from the patient and amplifies the radiation. Accordingly, it thereby permits the observation of the presently produced X-ray image either directly through an optical device associated with its outlet screen, or indirectly through the intermediary of a video system connected to the output thereof.

16 Claims, 6 Drawing Figures

DENTAL X-RAY DIAGNOSTIC INSTALLATION

FIELD OF THE INVENTION

The present invention relates to a dental X-ray diagnostic installation.

DISCUSSION OF THE PRIOR ART

A dental X-ray diagnostic apparatus is presently known possessing an X-ray tube arranged within a housing, and which includes a hollow anode introducible into the mouth of a patient. The hollow anode is encompassed by a cylinder-shaped applicator which is provided with a radiation outlet window from which there exits the X-radiation. Through the known X-ray diagnostic apparatus it is possible to undertake photographic surveys or charts of the upper jaw, the lower jaw, the jaw joints and the adjacent cavities. The preparation of an exposure is carried out in a manner in that the applicator, the latter of which is rotatable on the hollow anode, is brought into that position in which the X-radiation passes through the area of the patient which is to be photographed or X-rayed, the hollow anode together with the applicator being then inserted into the mouth, and that the patient applies the X-ray film to his face in the region which is to be X-rayed. The known X-ray diagnostic apparatus is thus only suited for the preparation of X-ray exposures and not for X-ray radioscopies in the jaw region.

SUMMARY OF THE INVENTION

Accordingly, it is an object of the present invention to so further equip and improve an apparatus of the above-mentioned type whereby, in addition to being suited for the preparation of X-ray exposures, it is also suited for effectuating X-ray radioscopies of the jaw region.

The foregoing object is inventively achieved in that the X-ray tube has an X-ray image intensifier associated therewith, and that means are provided which permit an alignment of its inlet screen with the focus of the X-ray tube. The X-ray image intensifier, during the carrying out of radioscopies, receives the X-radiation emanating from the patient and amplifies the radiation. Accordingly, it thereby permits the observation of the presently produced X-ray image either directly through an optical device associated with its outlet screen, or indirectly through the intermediary of a video system connected to the output thereof.

A suitable further construction of the invention consists of in that the image intensifier is fastened to a support which is rotatable about the axis of the X-ray tube. This support allows the X-ray image intensifier to be set to the region of the patient which is to be currently examined. It is particularly suitable that a protective cap, which is seated on the anode and rotatable with respect thereto about the longitudinal axis of the anode for radiation focusing (applicator), be so connected with the support so as to be taken along therewith during rotation of the support. During the adjustment of the X-ray image intensifier there is thus effected an automatic adjustment of the protective cap. A coordination with the current patient is possible when the image intensifier is connected with its support so as to be displaceable along the direction of the central beam of the X-radiation. Within the scope of the invention, the X-ray tube and the image intensifier may also be constructed as a unit which is freely held by the physician or dentist on a handgrip. Furthermore, it is possible that the X-ray image intensifier be constructed as a unit which is separate from the X-ray tube, which is manipulated by the physician separately from the X-ray tube, for example, held in the hand. Hereby, in order to render possible the satisfactory alignment of the X-ray image itensifier with the focus of the X-ray tube, it is thereby recommended that the X-ray tube housing be provided with orienting means for the aligning of the X-ray image intensifier. For instance, these orienting means may be a stop or a guide sleeve. Furthermore, for the case in which the X-ray tube housing is mechanically connected with the image intensifier, it is possible that for the adjustment of the X-ray tube together with its housing about the longitudinal axis of the image intensifier, it be pivotably connected with the image intensifier.

BRIEF DESCRIPTION OF THE DRAWINGS

Reference may now be had to the following detailed description of exemplary embodiments of the invention, taken in conjunction with the accompanying drawings; in which.

DETAILED DESCRIPTION

Figure 1:
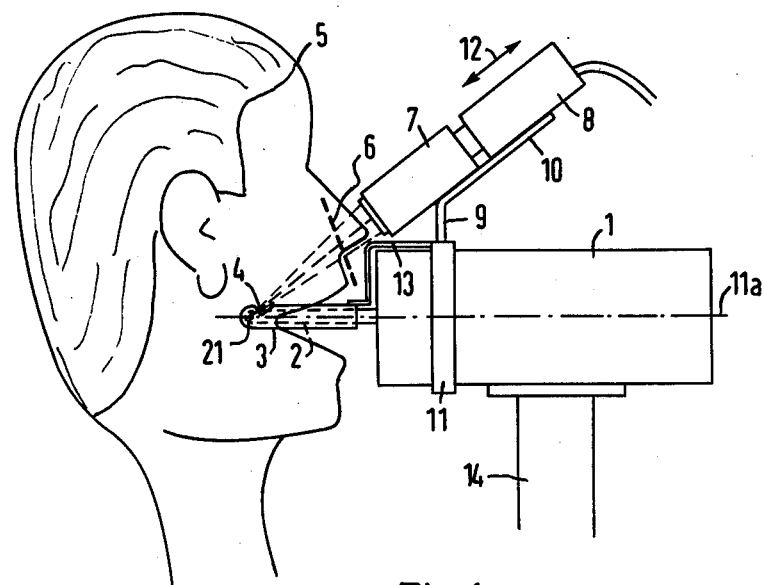
FIG. 1 schematically illustrates a dental X-ray diagnostic installation constructed pursuant to the present invention.

Referring now in detail to the drawings, in FIG. 1 there is shown an X-ray tube for dental X-ray radioscopies and exposures and the associated high-voltage transformer arranged within a housing 1. The X-ray tube possesses a hollow anode 2 which is able to be inserted into the mouth of the patient, and which is encompassed by a cylinder-shaped protective cap 3 serving for radiation focusing. The protective cap 3 possesses an aperture 4 through which there can egress the X-radiation, and is rotatable on the hollow anode 2 about the longitudinal axis of the latter. In the exemplary embodiment according to FIG. 1, the hollow anode 2 is inserted into the mouth of a patient 5. X-ray exposures can be prepared when a phantom-drawn X-ray film 6 is applied to the exterior of the face of the patient in the region which is to be X-rayed.

In order to undertake X-ray radioscopies there is provided an X-ray image intensifier 7 which has a television camera 8 connected to the output thereof. The X-ray intensifier 7 has its input screen aligned with the focus 21 of the X-ray tube. The unit 7, 8 is fastened to a support 9, the latter of which possesses a plate 10 which is rigidly interconnected with a ring 11. The unit 7, 8 is located on the plate 10 so as to be adjustable in the direction of the double-headed arrow 12, meaning in the direction of the central beam of the X-radiation, and thus can be set on the patient. The adjustment of the unit 7, 8 on the region of the patient 5 which is to be X-rayed is carried out through rotation of the ring 11 on the housing 1 about the axis 11a of the latter, and which also forms the axis of the X-ray tube and the anode 2. The ring 11 is connected with the protector cap 3 through intermediary of a coupling element 13 so that, upon rotation of the ring 11, the protector cap 3 is taken along and the window 4 similarly is automatically brought into the correct position. The ring 11 is lockable in position with respect to the housing 1. Furthermore, the unit 7, 8 is also lockable in position with respect to the plate 10.

The illustrated X-ray diagnostic apparatus allows the carrying out of dental X-ray radioscopic exposures. The X-ray image is hereby reproduced on a video viewing apparatus (not shown) which is controlled by the television camera 8. In lieu of the television camera 8 there may also be arranged a photographic film camera for the preparation of X-ray film pictures.

The housing 1 is mounted on a support column 14, the latter of which is supported on the floor in a manner not illustrated herein.

Figure 2:
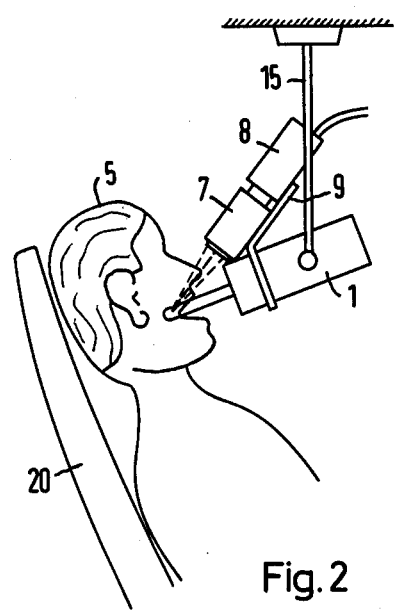
FIG. 2 illustrates the installation, drawn on a reduced scale, suspended from a ceiling support.

According to FIG. 2, the X-ray tube housing 1 which carries the image intensifier 7 and the television camera 8 through intermediary of the support 9, can also be suspended from a ceiling support 15.

Figure 3:
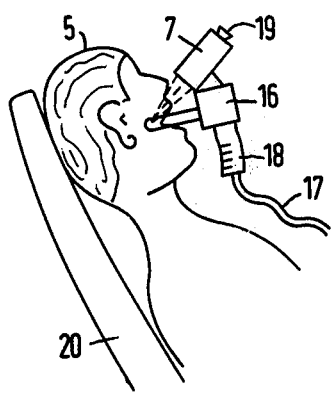
FIG. 3 illustrates a modified embodiment of the installation.

FIG. 3 illustrates an embodiment of the invention in which there is located in one housing 16 merely the hollow anode X-ray tube. The high-voltage transformer is arranged on the wall or on the floor externally of this housing, and a high-voltage conduit 17 leads from therethrough a hollow handgrip 18 to the X-ray tube in the housing 16. Connected with the housing 16, in accordance with the embodiment pursuant to FIG. 3, is the X-ray image intensifier 7, whose picture may be observed on the outlet or target screen through an optic device 19. The dentist can thereby hold the unit 7, 16 in his hand by means of handgrip 18 and insert the hollow anode into the mouth of the patient. On the handgrip 18 he can also bring the unit 7, 16 into the presently desired position, and observe the X-ray image through the optic device 19. In the examples according to FIGS. 2 and 3, the patient lies in a dental chair 20.

Figure 4:
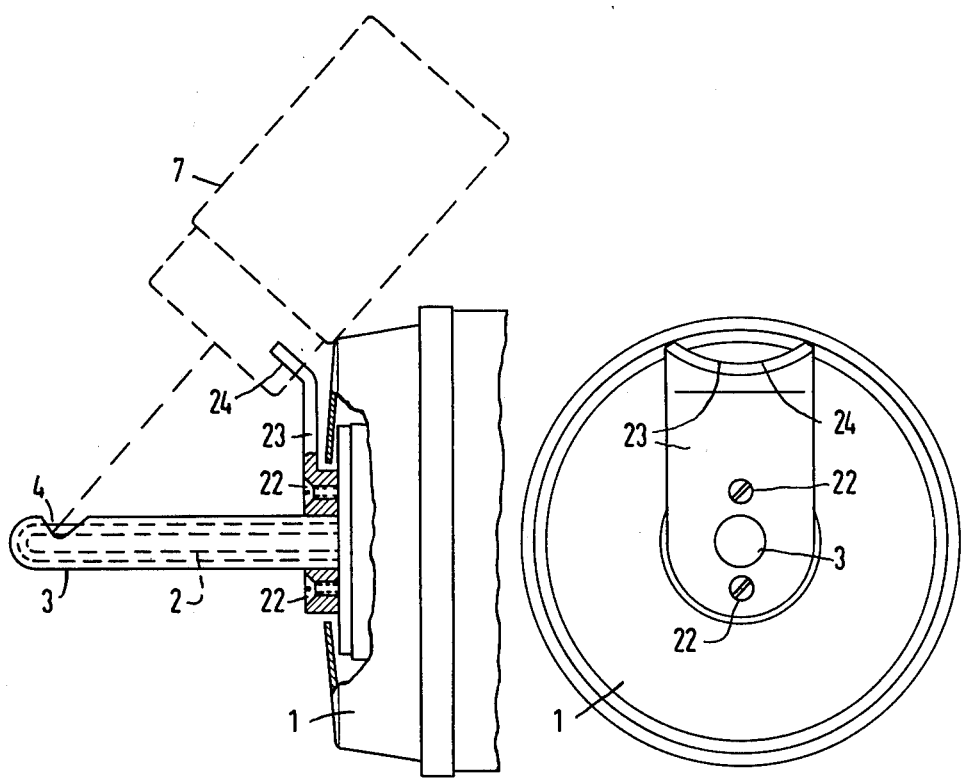
FIG. 4 illustrates an enlarged view of the inventive installation in which the X-ray image intensifier is constructed as a unit separate from the X-ray tube housing.

FIG. 4 illustrates an exemplary embodiment of the invention in which the X-ray image intensifier is constructed as a unit separate from the X-ray tube housing, in effect, can be manipulated by the physician independently of the X-ray tube in the housing 1. Mounted on the housing 1 by means of two screws 22 is an extension arm 23 which is provided with a recess 24 into which fits the image intensifier 7 with one end thereof. The recess 24 is clearly visible in the front view represented by FIG. 4. In this front view, the image intensifier has been omitted for purposes of clarity.

In order to undertake a radioscopy the physician guides the anode of the X-ray tube into the mouth of a patient, after he had slid on the protective cap 3 which possesses a radiation outlet aperture which is smaller than that of a protective cap which serves for the taking of X-ray exposures. Thereafter he positions the image intensifier 7 on the extension arm 23 and pivots it by hand in the desired direction.

Figure 5:
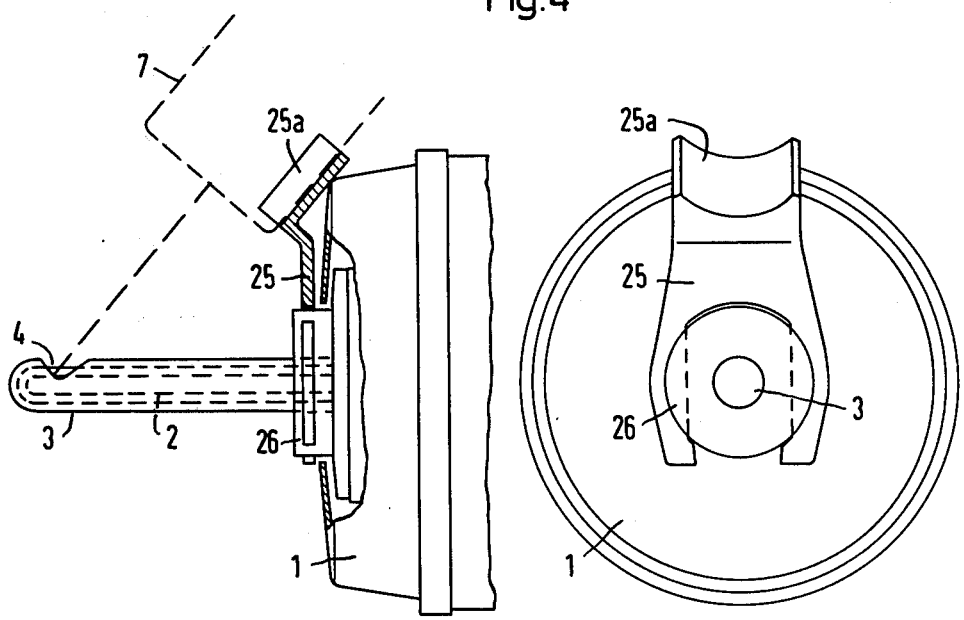
FIG. 5 illustrates a modified embodiment of the installation of FIG. 4.

The exemplary embodiment pursuant to FIG. 5 distinguishes from the exemplary embodiment shown in FIG. 3 in that an extension arm 25 is resiliently attached onto a projection 26 on the X-ray tube housing 1. For this purpose the projection 26 possesses suitable grooves.

The projection 25 is constructed as a portion of a cylindrical sleeve at its angled end 25a so as to thereby readily guide the image intensifier 7.

Figure 6:
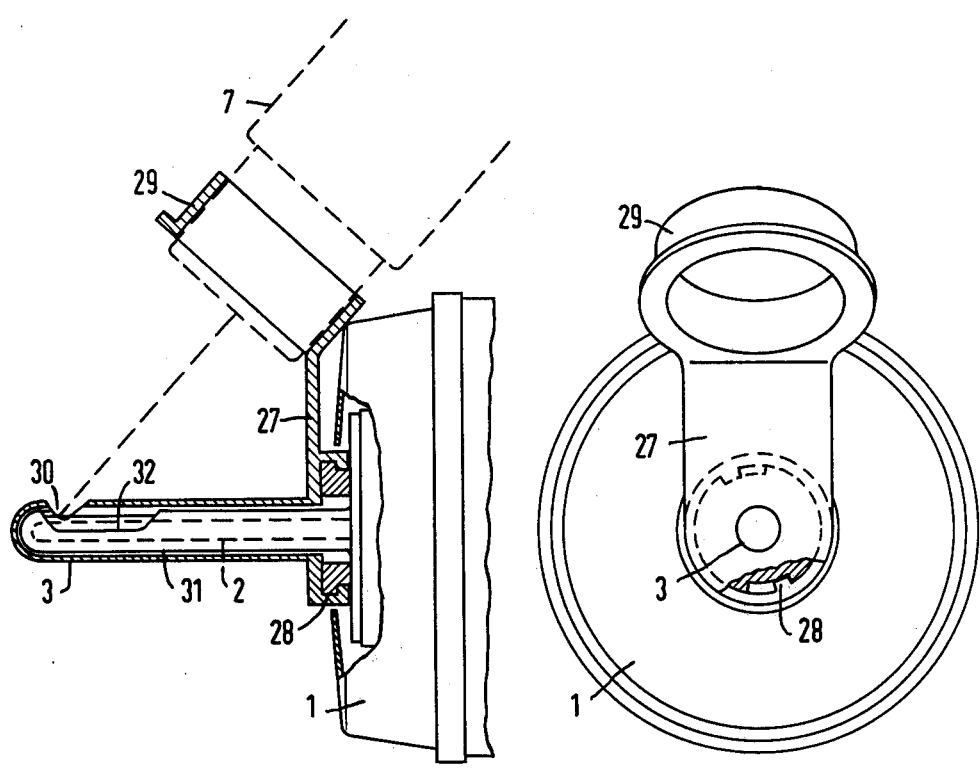
FIG. 6 illustrates a further embodiment of the inventive installation.

In the exemplary embodiment according to FIG. 6, an extension arm 27 is connected with the X-ray tube housing 1 by means of a bayonet lock 28, at whose end there is arranged a sleeve 29 in which there fits the image intensifier 7 with a close contact. This exemplary embodiment permits a particularly simple alignment of the image intensifier 7 with the focus of the X-ray tube. In the exemplary embodiment according to FIG. 6, the radiation protective cap 3 is fixedly connected with the extension arm 27. This radiation support cap, as described, possesses a small radiation outlet window 30 which is arranged for examination with an X-ray image intensifier. It is slid onto a radiation protective cap 31 which serves for the preparation of X-ray exposures, and which possesses a larger radiation outlet window 32. In order to undertake a dental X-ray radisocopy, in accordance with the exemplary embodiment of FIG. 6, the radiation protective cap 3 with the extension arm 27 is thus slid onto the radiation protective cap 31, and the bayonet lock 28 is secured. Thereafter, the image intensifier 7 can be slid into the guide sleeve 29.

The exemplary embodiments according to FIGS. 4 through 6 presently illustrate the side of the X-ray tube housing with the X-ray protective cap associated with the X-ray tube anode, and with the X-ray protective cap in, respectively, a partly sectioned side view and in a front view. In the exemplary embodiment according to FIG. 6, through the attachment of the components 3 and 27 it is possible to automatically actuate a switch which switches over at least one operative value for the X-ray tube, particularly the X-ray tube current, to the magnitude which is required for an image intensifier radioscopy.

While there has been shown what is considered to be the preferred embodiment of the invention, it will be obvious that modifications may be made which come within the scope of the disclosure of the specification.

What is claimed is:

1. In a dental X-ray diagnostic installation, an X-ray tube arranged within a housing; and said X-ray tube having an anode for insertion into the mouth of a patient, the improvement comprising: an X-ray image intensifier for receiving radiation from said X-ray tube, said X-ray image intensifier having an input screen; and means extending between the X-ray tube and image intensifier for aligning said input screen with the focus of said X-ray tube.

2. An installation as claimed in claim 1, said X-ray tube and said X-ray image intensifier being constructed of mutually separately manually manipulatable units; and said means for aligning being guide means for orientating said X-ray image intensifier to said X-ray tube, said guide means being located on said X-ray tube housing.

3. An installation as claimed in claim 2, said guide means being fixedly connected with said X-ray tube housing.

4. An installation as claimed in claim 2, said guide means being detachably connected with said X-ray tube housing.

5. An installation as claimed in claim 4, comprising an X-radiation screening protective cap having a radiation outlet window being fixedly connected with said guide means, said protective cap being slidable onto said anode.

6. An installation as claimed in claim 4, comprising a switch actuatable through said guide means for switching at least one operative value of the X-ray tube to a magnitude required for an image intensifier radioscopy.

7. An installation as claimed in claim 1, comprising a support mounting said X-ray tube, said support permitting pivoting of said X-ray tube about the longitudinal axis of said image intensifier.

8. An installation according to claim 1, wherein said means for aligning mechanically interconnects said image intensifier with said X-ray tube housing.

9. An installation as claims in claim 8, wherein said means for aligning includes a support mounting said image intensifier on the X-ray tube with said image intensifier being rotatable about the axis of said X-ray tube.

10. An installation as claimed in claim 9, comprising a protective cap seated on said anode and being rotatable relative thereto about the longitudinal axis of said anode for focusing of the radiation, said protective cap being mechanically connected to said support so as to be taken along with the latter upon rotation of said support.

11. An installation as claimed in claim 9, said X-ray image intensifier being connected with said support so as to be displaceable in the direction of the central beam of the X-radiation.

12. An installation as claimed in claim 8, comprising a floor-supported support column, said X-ray tube and said image intensifier being mounted on said support column.

13. An installation as claimed in claim 8, comprising a ceiling support, said X-ray tube and said image intensifier being suspended from said ceiling support.

14. An installation as claimed in claim 8, said X-ray tube and said image intensifier being a unit adapted to be held on a handgrip by a physician.

15. An installation as claimed in claim 1, said image intensifier including optic means for viewing the image on its output target screen.

16. An installation as claimed in claim 14, comprising a high-voltage conduit for said X-ray tube extending through said handgrip.

* * * * *